United States Patent [19]

Mita et al.

[11] Patent Number: 4,612,388

[45] Date of Patent: Sep. 16, 1986

[54] PROCESS FOR PRODUCING N-ACYLPHENYLALANINES

[75] Inventors: Ryuichi Mita; Toshio Katoh, both of Kawasaki; Chojiro Higuchi; Akihiro Yamaguchi, both of Kamakura, all of Japan

[73] Assignee: Mitsui Toatsu Chemicals, Incorporated, Tokyo, Japan

[21] Appl. No.: 719,300

[22] Filed: Apr. 3, 1985

[30] Foreign Application Priority Data

Apr. 10, 1984 [JP] Japan ................................. 59-69999

[51] Int. Cl.$^4$ ............................................. C07C 99/06
[52] U.S. Cl. ................... 562/443; 562/444; 562/445; 562/446; 562/447; 549/441
[58] Field of Search ............... 562/443, 444, 445, 446, 562/447; 549/441

[56] References Cited

U.S. PATENT DOCUMENTS

| | | | |
|---|---|---|---|
| 2,678,313 | 5/1954 | Heilbron et al. | 562/443 |
| 3,085,111 | 4/1963 | Meltzer | 562/447 |
| 3,329,711 | 7/1967 | Hegedus et al. | 562/446 |
| 3,544,623 | 12/1970 | Hansen et al. | 562/445 |
| 4,261,919 | 4/1981 | Knowles et al. | 562/443 |
| 4,508,921 | 4/1985 | Amato et al. | 562/443 |

*Primary Examiner*—James H. Reamer

*Attorney, Agent, or Firm*—Oblon, Fisher, Spivak, McClelland & Maier

[57] ABSTRACT

Disclosed herein is a process for producing an N-acyl-substituted or unsubstituted phenylalanine comprising hydrolyzing a 2-substituted-4-substituted or unsubstituted benzylidene-5-oxazolone with alkali, adjusting pH of the reaction solution containing its hydrolysis product with acid at 5–9 and reducing the resultant reaction solution catalytically in the presence of a palladium or platinum reducing catalyst.

In accordance with the process of the present invention, time duration required for effecting the reduction can be shortened markedly in comparison with the reduction in an aqueous strong alkaline solution. Moreover, the catalyst recovered after completion of the reduction can be used repeatedly without any additional treatment and without any observed lowering in its activity. Accordingly, the reduction using the recovered catalyst may proceed in practically the same time as in the case of using a fresh catalyst.

In the process of the present invention, the reduction is carried out continuously without isolating the alkaline hydrolysis product, i.e., a substituted or unsubstituted N-acylaminocinnamic acid from the reaction mixture, so that the process is featured advantageously by simplified process and improved overall yield.

15 Claims, No Drawings

4,612,388

PROCESS FOR PRODUCING N-ACYLPHENYLALANINES

DESCRIPTION

1. Technical Field

This invention relates to a process for producing substituted or unsubstituted N-acylphenylalanines.

2. Background Art

N-acylphenylalanines are important compounds as precursors of phenylalanines. Particularly, unsubstituted N-acylphenylalanines are categorized as essential amino acids and are important compounds as precursors of L-phenylalanine which has come to be rapidly used as a starting material of an artificial sweetener "Aspartame". For example, N-acetylphenylalanine readily undergoes asymmetric hydrolysis by the action of an enzyme acylase to form L-phenylalanine.

Conventionally, N-acylphenylalanines have generally been produced by the reduction of either 2-substituted-4-(substituted) benzylidene-5-oxazolones which are produced relatively easily by condensation reaction of an N-acylglycine and a benzaldehyde or α-acylaminocinnamic acids which are hydrolysis products of said oxazolones. Although a variety of processes have hitherto been proposed for effecting the reduction, it is practical in an industrial sense to carry out the reduction catalytically in the presence of a heterogeneous reducing catalyst. For example, in accordance with the method of T. Okuda and Y. Fujii (Bull. Chem. Soc. (Japan), 30, 698 (1957)), a substituted or unsubstituted 2-methyl-4-benzylidene-5-oxazolone is reduced catalytically in an alkaline solution under a pressure of 40–70 kg/cm² using Raney nickel as a catalyst to produce an N-acetylphenylalanine. As an example of using a heterogeneous catalyst of noble metal, there is disclosed a method by R. M. Herbst and D. Shemin (Organic Synthesis, Coll. Vol. 2, p491) wherein α-acetylaminocinnamic acid is reduced catalytically in acetic acid under atomspheric pressure using platinum oxide as a catalyst to produce N-acetylphenylalanine.

However, since the former method carries out the reduction under a high pressure, there is imposed a restriction on the apparatus that is used in effecting the method industrially. Moreover, the Raney nickel used in a relatively large amount raises environmental problems in its disposal. Further, the latter method which uses acetic acid as a solvent is accompanied by such a drawback that its operation is complicated because the solvent has to be concentrated or distilled upon isolation of the product after the reduction.

Recently, noble metals such as palladium or platinum have come to be used frequently also on industrial scale as a catalyst for use in catalytic reduction. This is because these catalysts are effective in a relatively small amount, are recovered easily because they are heterogeneous to various solvents, and eliminate environmental problems caused by disposal because they are regenerative, although they are extremely expensive. These expensive noble metal catalysts are generaly used repeatedly in industry by way of their recovery after completion of reaction.

The present inventors have hydrolyzed 2-methyl-4-benzylidene-5-oxazolone with alkali in water and reduced catalytically the resultant α-acetylaminocinnamic acid, without isolating it from the reaction solution, by adding a palladium or platinum reducing catalyst thereto to prepare N-acetylphenylalanine. Then, it was found that the catalyst recovered by filtration after the reduction was lowered in catalytic activity through its repeated use, thus requiring a considerably longer time in effecting the reduction as opposed to the case using a fresh catalyst, and finally lost its activity almost completely through several times of its repeated use. The same situation was occurred when other 2-substituted-4-(substituted)benzylidene-5-oxazolones were used. Further, it was also found that a catalyst having been lowered or lost in activity could not be recovered in catalytic activity even by washing it with an organic solvent such as alcohol or with an acid such as dilute hydrochloric acid and thus its catalytic activity was irreversible.

On the basis of these experimental facts, the present inventors have made an intensive effort to establish a process for the preparation of N-acylphenylalanines from 2-substituted-4-(substituted)benzylidene-5-oxazolones wherein a reducing catalyst can be used efficiently and repeatedly without lowering or losing its catalytic activity during the reduction. As a result, it was found that pH of the reaction solution during the reduction was closely related to the activity of the catalyst and therefore was responsible for the irreversible decrease in activity of the recovered catalyst, thus leading to the completion of the present invention.

DISCLOSURE OF THE INVENTION

Specifically, the present invention provides a process for producing N-acylphenylalanines represented by the general formula (II):

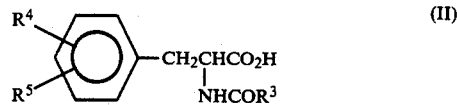

wherein $R^4$ and $R^5$ independently of one another are a hydrogen atom, an alkyl group having 1–4 carbon atoms, an alkoxy group having 1–4 carbon atoms, a halogen atom, a hydroxyl group or an aryloxy group, or adjoiningly to each other and together are a methylenedioxy group, and $R^3$ is a methyl or phenyl group which process comprises hydrolyzing 2-substituted-4-(substituted)benzylidene-5-oxazolones represented by the general formula (I):

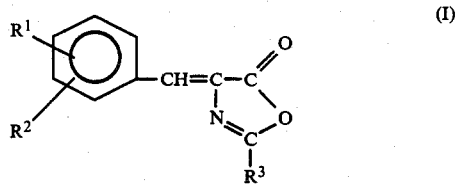

wherein each $R^1$ and $R^2$ independently of one another are a hydrogen atom, an alkyl group having 1–4 carbon atoms, an alkoxy group having 1–4 carbon atoms, a halogen atom, an acyloxy group or an aryloxy group, or adjoiningly to each other and together are a methylenedioxy group, and $R^3$ is a methyl or phenyl group with alkali, adjusting pH of the reaction solution containing the hydrolysis product at 5–9 with acid and subjecting the resultant reaction solution to catalytic reduction in the presence of a palladium or platinum reducing catalyst.

In accordance with the process of the present invention, the time period required for the reduction can be remarkably shortened as compared with the reduction in an aqueous strong alkaline solution. Moreover, there is such a great advantage in the present process that the catalyst recovered through filtration after the reduction can be used repeatedly without any additional treatment and without any observed decrease in its catalytic activity so that the reduction using the recovered catalyst may proceed in practically the same time duration as in the case of using a fresh catalyst. Further, in the process of the present invention, the starting material, 2-substituted-4-(substituted)benzylidene-5-oxazolone, is hydrolyzed with alkali to produce a substituted or unsubstituted N-acylaminocinnamic acid which is subsequently and continuously subjected to the reduction without being isolated from the reaction mixture. Accordingly, the present process has advantages over a process wherein a N-acylaminocinnamic acid is reduced after it has been isolated from the reaction system in such a regard as simplified process and improved overall yield.

BEST MODE FOR CARRYING OUT THE INVENTION

The process of the present invention comprises two steps consisting of treating a 2-substituted-4-(substituted)benzylidene-5-oxazolone represented by the general formula (I) with alkali to form a substituted or unsubstituted α-acylaminocinnamic acid and reducing catalytically the resultant α-acylaminocinnamic acid without isolating it from the reaction system.

Specific examples of the 2-substituted-4-(substituted)-benzylidene-5-oxazolone of the general formula (I) used as the starting material in the present process include
2-methyl-4-benzylidene-5-oxazolone,
2-phenyl-4-benzylidene-5-oxazolone,
2-methyl-4-(p-methylbenzylidene)-5-oxazolone,
2-phenyl-4-(p-methylbenzylidene)-5-oxazolone,
2-methyl-4-(p-ethylbenzylidene)-5-oxazolone,
2-phenyl-4-(p-iso-propylbenzylidene)-5-oxazolone,
2-methyl-4-(p-n-butylbenzylidene)-5-oxazolone,
2-methyl-4-(p-methoxybenzylidene)-5-oxazolone,
2-phenyl-4-(p-methoxybenzylidene)-5-oxazolone,
2-methyl-4-(3,4-dimethoxybenzylidene)-5-oxazolone,
2-methyl-4-(2,3-dimethoxybenzylidene)-5-oxazolone,
2-phenyl-4-(2,4-dimethoxybenzylidene)-5-oxazolone,
2-methyl-4-(3,5-dimethoxybenzylidene)-5-oxazolone,
2-methyl-4-(p-ethoxybenzylidene)-5-oxazolone,
2-methyl-4-(3,4-diethoxybenzylidene)-5-oxazolone,
2-phenyl-4-(p-n-propoxybenzylidene)-5-oxazolone,
2-methyl-4-(p-n-butoxybenzylidene)-5-oxazolone,
2-methyl-4-(p-chlorobenzylidene)-5-oxazolone,
2-phenyl-4-(p-chlorobenzylidene)-5-oxazolone,
2-methyl-4-(3,4-dichlorobenzylidene)-5-oxazolone,
2-phenyl-4-(3,4-dichlorobenzylidene)-5-oxazolone,
2-methyl-4-(m-phenoxybenzylidene)-5-oxazolone,
2-phenyl-4-(m-phenoxybenzylidene)-5-oxazolone,
2-methyl-4-(p-acetoxybenzylidene)-5-oxazolone,
2-phenyl-4-(p-acetoxybenzylidene)-5-oxazolone,
2-methyl-4-(3,4-diacetoxybenzylidene)-5-oxazolone,
2-phenyl-4-(3,4-diacetoxybenzylidene)-5-oxazolone,
2-methyl-4-(3,4-methylenedioxybenzylidene)-5-oxazolone or
2-phenyl-4-(3,4-methylenedioxybenzylidene)-5-oxazolone.

These starting materials can easily be produced by the Erlenmeyer method in which N-acetylglycine or N-benzoylglycine (hippuric acid) is condensed with a substituted or unsubstituted benzaldehyde in acetic anhydride in the presence of anhydrous sodium acetate or the method in which a β-phenylserine is treated in acetic anhydride in the presence of a base (Japanese Patent Application Laid-Open No. 32753/1985).

The first step of the process of the present invention, in which an α-acylaminocinnamic acid is produced through hydrolysis of a 2-substituted-4-(substituted)-benzylidene-5-oxazolone, comprises treating said starting material present in an aqueous medium in the state of suspension or solution by adding thereto an alkali such as hydroxide, oxide or carbonate of an alkali or alkaline earth metal in amount in excess of its stoichiometric requirement, thereby producing a corresponding α-acylaminocinnamic acid easily. The amount of water thereby used is one part by weight or more, or preferably two parts by weight or more from an operational standpoint, per one part by weight of the starting material, 2-substituted-4-(substituted)benzylidene-5-oxazolone. The temperature and time duration applied in the hydrolysis are 0°–100° C. and 0.5–20 hours, or preferably 20°–80° C. and 1–15 hours, respectively. An aqueous solution of an alkali or alkaline earth metal salt of an α-acylaminocinnamic acid is obtained in the above manner. However, in a case where an acyloxy group-substituted oxazolone is used as the starting material, the acyloxy group will also be hydrolyzed to form a hydroxyl group-substituted α-acylaminocinnamic acid. In the hydrolysis of 2-substituted-4-(substituted)benzylidene-5-oxazolones, various water-miscible organic solvents, for example, methanol, ethanol, isopropanol, acetone, dioxane, tetrahydrofuran or the like, may be used jointly without raising any problems. However, the hydrolysis reaction proceeds under mild conditions even in a water medium. In addition, it is sometimes necessary to distill or remove the organic solvent in the isolation of the intended compound of N-acylphenylalanine after completion of the subsequent catalytic reduction, with the result that the post-reaction treatment is made complicated. From these point of view, it is not necessary to daringly use the organic solvent jointly.

In the second step of the process of the present invention, the reaction solution containing an alkaline salt of an α-acylaminocinnamic acid which results from the foregoing first step is adjusted in pH at 5–9 and thereafter it is subjected to catalytic reduction in the presence of a palladium or platinum reducing catalyst to produce an N-acylphenylalanine.

Upon effecting the catalytic reduction of this step, the reaction solution containing an alkaline salt of an α-acylaminocinnamic acid obtained from the alkaline hydrolysis of a 2-substituted-4-(substituted)benzylidene-5-oxazolone is neutralized with an acid to adjust its pH in the range of 5–9 or preferably 5.5–8.5 and subsequently added with a reducing catalyst so as to be subjected to catalytic reduction. Although hydrochloric and sulfuric acids are frequently used as the acid for the pH adjustment, there may also be used, as a matter of course, other mineral acids or organic acids such as acetic acid and p-toluenesulfonic acid. If pH of the reaction solution should exceed 9 during the reduction period, catalytic activity of the recovered catalyst will, as pointed out previously, be lowered or lost through its repeated use, and even in the case of using a fresh catalyst, the reaction time duration will tend to be prolonged as opposed to the reduction in the pH range defined in the present invention. Further, if the pH should be as low as less than 5, solubility of the N-acylaminocinnamic acid will be decreased and thus the reduction will have to be carried out in the state of suspension so that the time duration for completion of the reaction will unfavorably be prolonged.

Any type of noble metal catalyst of palladium or platinum series can be used as the reducing catalyst so far as it makes up a heterogenous catalytic system to the reaction solution. Specific examples of such catalysts may include palladium-carbon, palladium black, colloidal palladium, palladium-barium sulfate, palladium-alumina, platinum oxide, platinum-carbon or platinum-silica gel. Needless to say, it should not be construed that the catalyst used in the present invention is limited only to these exemplary catalysts. The amount of the catalyst to be used is generally 0.1% by weight or more based on the starting material, 2-substituted-4-(substituted)benzylidene-5-oxazolone, and besides, the larger the amount to be used, the shorter will be the time duration required for the reduction. However, from economical and operational point of view, it is preferred to use the catalyst in an amount of 30% by weight or less. More favorably, it is recommended to use it in an amount in the range of 0.5–10% by weight.

The temperature and the time duration of the reduction depend more or less on the amount of the catalyst used but generally lie in the ranges of 0°–100° C. and 0.5–30 hours, respectively. The reduction may be effected either under atmospheric pressure or under pressure.

Since N-acylphenylalanines are generally dissolved in the reaction solution after completion of the reaction, it is possible, as required, to isolate the N-acylphenylalanines from the reaction solution by filtering and removing the catalyst while the reaction solution is hot and thereafter acidifying the filtrate with an acid such as hydrochloric acid. The catalyst thus-recovered can be used repeatedly, maintaining its original activity to effect the reduction without any further treatment and without any observed lowering in its catalytic activity.

The present invention will be described more specifically with reference to the following examples.

EXAMPLE 1

In a 100-ml tightly-sealed glass vessel were charged 9.36 g of 2-methyl-4-benzylidene-5-oxazolone and 30 ml of water. Thereafter, 5.3 g of 45% sodium hydroxide solution was added thereto and the resulting mixture was stirred at 40°–45° C. for 2 hours. The 2-methyl-4-benzylidene-5-oxazolone was hydrolyzed to form an aqueous homogeneous solution of sodium α-acetylaminocinnamate. Then, concentrated hydrochloric acid was added to the solution to adjust its pH at 7.2, and subsequently 0.2 g of 5%-palladium-carbon was added thereto. The gas phase in the vessel was purged with nitrogen and then with hydrogen and thereafter the content in the vessel was subjected to catalytic reduction at 40°–45° C. under atmospheric pressure. The reaction time was approximately 90 minutes until hydrogen absorption was completed. During this time period, it was observed that one mole of hydrogen was absorbed to one mole of 2-methyl-4-benzylidene-5-oxazolone.

The gas phase in the vessel was purged with nitrogen after completion of the reaction and thereafter the catalyst was filtered and washed with a small amount of water. The filtrate and the washings were combined and concentrated hydrochloric acid was added thereto at 30°–35° C. to adjust pH of the resultant mixture at 1. The mixture was then cooled to 0°–5° C. The crystal was filtered, washed with a cold water and dried to obtain 9.96 g of N-acetylphenylalanine as a white crystal. Its yield was 96.1% based on the 2-methyl-4-benzylidene-5-oxazolone. Its melting point was 150.5°–151° C.

EXAMPLE 2

In the same manner as in Example 1, 2-methyl-4-benzylidene-5-oxazolone was treated with alkali to obtain an aqueous solution of sodium N-acetylaminocinnamate which was then subjected to reduction after adjusting its pH with concentrated hydrochloric acid at 7.2 using the palladium-carbon catalyst recovered in Example 1 without any further treatment. The catalyst was used repeatedly five times for effecting the reduction. Results are shown in Table 1. In each of the repeated experiments, the reduction was completed in 95–105 minutes. This signifies in comparison with Example 1 that each reduction time was not practically affected by the repeated use of catalyst.

TABLE 1

Results of the repeated use of catalyst

| Number of repeated times (No.) | Time required for reduction (minutes) | N—acetylphenylalanine Amount (g) | Melting point (°C.) | Yield (%) |
|---|---|---|---|---|
| 1 | 100 | 9.94 | 150–151 | 95.9 |
| 2 | 95 | 10.05 | " | 97.0 |
| 3 | 95 | 9.89 | " | 95.5 |
| 4 | 105 | 9.92 | 149.5–151 | 95.8 |
| 5 | 100 | 9.82 | 150–151 | 94.8 |

COMPARATIVE EXAMPLE 1

In a 100-ml tightly-sealed glass vessel were charged 9.36 g of 2-methyl-4-benzylidene-5-oxazolone and 30 ml of water. Then, 5.3 g of 45% sodium hydroxide solution was added thereto and the resulting mixture was stirred at 40°–45° C. for two hours. The 2-methyl-4-benzylidene-5-oxazolone was hydrolyzed to form an aqueous homogeneous solution of sodium α-acetylaminocinnamate. The solution had a pH in excess of 12. 0.2 g of 5%-palladium-carbon was then added to the solution. After the gas phase in the vessel was purged with nitrogen and then with hydrogen, the reaction mixture in the vessel was subjected to catalytic reduction at 40°–45° C. under atmospheric pressure. The time required for the reduction was approximately four hours. After completion of the reduction, the reaction mixture was treated in the same manner as in Example 1 to obtain 9.91 g of N-acetylphenylalanine as a white crystal. Its melting point was 149.5°–150.5° C.

COMPARATIVE EXAMPLE 2

Procedures of Comparative Example 1 were repeated to effect the reaction except for the repeated use of the catalyst recovered in Comparative Example 1. The time durations required for the reduction were 6.5 hours and 10 hours for the first and second repeated uses, respectively. In the third repeated use, hydrogen absorption was interrupted during the reduction.

EXAMPLES 3 AND 4

Each example was effected in the same manner as in Example 1 except that pH of the solution during the reduction was changed. Results are shown in Table 2.

The each catalyst recovered in these two experiments was used repeatedly three times under the same conditions, respectively. The time durations required for the reduction of these repetitions were practically the same as that resulted when a fresh catalyst was used.

TABLE 2

| Example No. | pH during reduction | Time required for reduction (minutes) |
|---|---|---|
| 3 | 8.5 | 125 |
| 4 | 5.5 | 110 |

EXAMPLE 5

In 100-ml tightly-sealed glass vessel were charged 9.36 g of 2-methyl-4-benzylidene-5-oxazolone and 40 ml of water. 4.15 g of potassium carbonate was then added thereto and the resulting mixture was stirred at 40°–45° C. for two hours. Concentrated hydrochloric acid was added to the resulting solution to adjust its pH at 6.8 and 0.2 g of 5%-palladium-carbon was added thereto. The gas phase in the vessel was purged with nitrogen and then with hydrogen, and thereafter the reaction mixture in the vessel was subjected to catalytic reduction at 40°–45° C. under atmospheric pressure. The reaction time during which hydrogen absorption was completed was 100 minutes. It was observed that one mole of hydrogen was absorbed to one mole of 2-methyl-4-benzylidene-5-oxazolone during this period. After the gas phase in the vessel was purged with nitrogen upon completion of the reaction, the catalyst was filtered and washed with a small amount of water. The filtrate and the washings were combined, to which concentrated hydrochloric acid was added at a temperature lower than 30° C. to adjust pH of the resulting mixture at 1. The mixture was cooled to 0°–5° C. The crystal was filtered, washed with a cold water and dried to obtain 9.81 g of N-acetylphenylalanine having a melting point 150°–151° C. as a white crystal. Its yield was 94.7%.

Using the foregoing recovered catalyst repeatedly, experiments were carried out three times under the same conditions as described above. In each of the experiments, the time duration required for the reduction was in the range of 95–110 minutes which was practically the same as in the case of using a fresh catalyst.

EXAMPLES 6 TO 12

0.05 mole of each of various 2-substituted-4-(substituted)benzylidene-5-oxazolones was suspended in 40–100 ml of water and 5.3 g of 45% sodium hydroxide solution was added thereto to hydrolyze it at 40°–80° C. for 1–3 hours, thereby forming a corresponding α-acylaminocinnamic acid. Then, concentrated hydrochloric acid was added to the resultant aqueous solution to adjust its pH at 5.5–8.5. The resultant solution was charged into a tightly-sealed glass vessel. 5%-palladium-carbon was added thereto and the gas phase in the vessel was purged with nitrogen and with hydrogen. Thereafter, the reaction mixture was subjected to catalytic reduction under atmospheric pressure. Procedures of Example 1 were repeated in the isolation of each of N-acylphenylalanines resulted from the reduction. Results are shown in Table 3.

TABLE 3

| Exp. No. | 2-Substituted-4-(substituted)benzylidene-5-oxazolone R¹ | R² | R³ | water (ml) | catalyst (g) | pH during reduction | Reduction temperature (°C.) | Reduction time (min) | N—acylphenylalanine Compound name | Amount (g) | Melting point (°C.) |
|---|---|---|---|---|---|---|---|---|---|---|---|
| 6 | H | H | —⟨O⟩ | 60 | 0.25 | 6.9 | 40–45 | 105 | N—benzoylphenylalanine | 13.2 | 186.5–187 |
| 7 | H | p-CH₃ | CH₃ | 40 | 0.12 | 7.4 | " | 140 | N—acetyl-p-methylphenylalanine | 10.4 | 164–165 |
| 8 | H | p-OCH₃ | CH₃ | " | 0.20 | 7.1 | " | 95 | N—acetyl-p-methoxyphenylalanine | 11.2 | 150.5–151.5 |
| 9 | 3,4-CH₂⟨O—, O—⟩ | | CH₃ | 50 | 0.21 | 7.3 | 50–55 | 50 | N—acetyl-3,4-methylenedioxyphenylalanine | 12.5 | 166–167 |
| 10 | H | p-Cl | CH₃ | " | 0.23 | 7.3 | " | 60 | N—acetyl-p-chlorophenylalanine | 11.7 | 183–184 |
| 11 | H | m—⟨O⟩—O— | CH₃ | 100 | 0.2 | 7.0 | 60–65 | 80 | N—acetyl-p-phenoxyphenylalanine | 14.7 | 146–147 |
| 12:ᵃ | H | p-CH₃COO— | CH₃ | 40 | 0.2 | 7.3 | 40–45 | 90 | N—acetyl-p-hydroxyphenylalanine | 9.1 | 92–93 |

*ᵃThe amount of 45% sodium hydroxide solution used during the hydrolysis was 10.7 g.

We claim:

1. A process for producing an N-acylphenylalanine compound of formula (II):

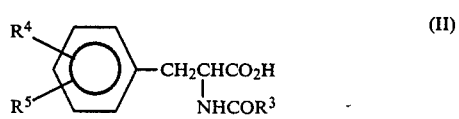

(II)

wherein R⁴ and R⁵ independently of each other are hydrogen, an alkyl group having 1–4 carbon atoms, an alkoxy group having 1–4 carbon atoms, halogen, hydroxyl, or aryloxy, or together form a methylenedioxy group, and R³ is methyl or phenyl, which comprises:

(a) hydrolyzing a 2-substituted-4-(substituted)benzylidene-5-oxazolone compound of formula (I):

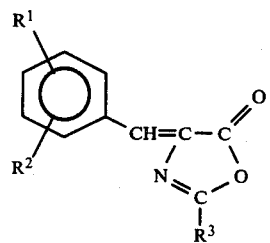

(I)

wherein R¹ and R² independently of each other are hydrogen, an alkyl group having 1–4 carbon atoms, an alkoxy group having 1–4 carbon atoms, halogen, acyloxy or aryloxy, or together form a methylenedioxy group, and R³ is as defined above, with alkali in an aqueous medium;
(b) adjusting the pH of the aqueous reaction solution containing the hydrolysis product with acid to within the range of 5–9;
(c) adding a platinum or palladium reducing catalyst to the pH adjusted aqueous solution; and
(d) subjecting the hydrolysis product in said resultant reaction solution to catalytic reduction, thereby producing said N-acylphenylalanine product.

2. The process of claim 1, wherein said 2-substituted-4-(substituted)benzylidene-5-oxazolone starting material is a member selected from the group consisting of 2-methyl-4-benzylidene-5-oxazolone, 2-phenyl-4-benzylidene-5-oxazolone, 2-methyl-4-(p-methyl-benzylidene)-5-oxazolone, 2-phenyl-4-(p-methylbenzylidene)-5-oxazolone, 2-methyl-4-(p-ethylbenzylidene)-5-oxazolone, 2-phenyl-4-(p-isopropylbenzylidene)-5-oxazolone, 2-methyl-4-(p-n-butylbenzylidene)-5-oxazolone, 2-methyl-4-(p-methoxybenzylidene)-5-oxazolone, 2-phenyl-4-(p-methoxybenzylidene)-5-oxazolone, 2-methyl-4-(3,4-dimethoxybenzylidene)-5-oxazolone, 2-methyl-4-(2,3-dimethoxybenzylidene)-5-oxazolone, 2-phenyl-4-(2,4-dimethoxybenzylidene)-5-oxazolone, 2-methyl-4-(3,5-dimethoxybenzylidene)-5-oxazolone, 2-methyl-4-(p-ethoxybenzylidene)-5-oxazolone, 2-methyl-4-(3,4-diethoxybenzylidene)-5-oxazolone, 2-phenyl-4-(p-n-propoxybenzylidene)-5-oxazolone, 2-methyl-4-(p-n-butoxybenzylidene)-5-oxazolone, 2-methyl-4-(p-chlorobenzylidene)-5-oxazolone, 2-phenyl-4-(p-chlorobenzylidene)-5-oxazolone, 2-methyl-4-(3,4-dichlorobenzylidene)-5-oxazolone, 2-phenyl-4-(3,4-dichlorobenzylidene)-5-oxazolone, 2-methyl-4-(m-phenoxybenzylidene)-5-oxazolone, 2-phenyl-4-(m-phenoxybenzylidene)-5-oxazolone, 2-methyl-4-(p-acetoxybenzylidene)-5-oxazolone, 2-phenyl-4-(p-acetoxybenzylidene)-5-oxazolone, 2-methyl-4-(3,4-diacetoxybenzylidene)-5-oxazolone, 2-phenyl-4-(3,4-diacetoxybenzylidene)-5-oxazolone, 2-methyl-4-(3,4-methylenedioxybenzylidene)-5-oxazolone and 2-phenyl-4-(3,4-methylenedioxybenzylidene)-5-oxazolone.

3. The process of claim 1, wherein the alkali of said aqueous hydrolysis medium is a hydroxide, oxide or carbonate of an alkali metal or alkaline earth metal.

4. The process of claim 1, wherein the amount of water in the aqueous reaction medium of step (a) is at least one part by weight per part by weight of the oxazolone starting material.

5. The process of claim 1, wherein the hydrolysis reaction is conducted at a temperature of 0°–100° C. for 4.5–20 hours.

6. The process of claim 5, wherein said hydrolysis is conducted at a temperature of from 20°–80° C. for 1–15 hours.

7. The process of claim 1, wherein the aqueous reaction medium contains a water-miscible organic solvent selected from the group consisting of methanol, ethanol, isopropanol, acetone, dioxane or tetrahydrofuran.

8. The process of claim 1, wherein, in step (b), the pH of the aqueous medium is adjusted to within the range of 5.5–8.5.

9. The process of claim 1, wherein the pH of the aqueous medium of step (b) is adjusted by the addition of hydrochloric acid, sulfuric acid, acetic acid or p-toluenesulfonic acid thereto.

10. The process of claim 1, wherein said platinum or palladium catalyst is selected from the group consisting of palladium-carbon, palladium black, colloidal palladium, palladium-barium sulfate, palladium-alumina, platinum oxide, platinum-carbon and platinum-silica gel.

11. The process of claim 1, wherein said catalyst is present in an amount of at least 0.1% by weight based on the amount of oxazolone starting material.

12. The process of claim 1, wherein the amount of catalyst does not exceed 30% by weight based on the weight of said oxazolone starting material.

13. The process of claim 1, wherein the amount of said catalyst ranges from 0.5–10% by weight based on said oxazolone starting material.

14. The process of claim 1, wherein the reduction process of step (d) is conducted at a temperature within the range of 0°–100° C. for 0.5–30 hours.

15. The process of claim 1, wherein said reduction is conducted under atmospheric pressure or elevated pressure.

* * * * *